(12) United States Patent
Moore et al.

(10) Patent No.: US 9,029,403 B2
(45) Date of Patent: May 12, 2015

(54) TREATMENT OF OVARIAN CANCER WITH BENZYLIDENEBENZOHYDRAZIDES

(71) Applicant: Memorial Sloan-Kettering Cancer Center, New York, NY (US)

(72) Inventors: Malcolm Moore, New York, NY (US); Server A. Ertem, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/357,429

(22) PCT Filed: Nov. 9, 2012

(86) PCT No.: PCT/US2012/064278
§ 371 (c)(1),
(2) Date: May 9, 2014

(87) PCT Pub. No.: WO2013/071001
PCT Pub. Date: May 16, 2013

(65) Prior Publication Data
US 2014/0315959 A1     Oct. 23, 2014

Related U.S. Application Data

(60) Provisional application No. 61/558,293, filed on Nov. 10, 2011.

(51) Int. Cl.
| | |
|---|---|
| C07D 307/68 | (2006.01) |
| A61K 31/166 | (2006.01) |
| A61K 31/341 | (2006.01) |
| A61K 31/415 | (2006.01) |
| A61K 31/44 | (2006.01) |
| C07D 213/87 | (2006.01) |
| C07C 243/38 | (2006.01) |
| C07D 213/82 | (2006.01) |
| C07D 231/12 | (2006.01) |

(52) U.S. Cl.
CPC ............ *C07D 307/68* (2013.01); *A61K 31/166* (2013.01); *A61K 31/341* (2013.01); *A61K 31/415* (2013.01); *A61K 31/44* (2013.01); *C07D 213/87* (2013.01); *C07C 243/38* (2013.01); *C07D 213/82* (2013.01); *C07D 231/12* (2013.01)

(58) Field of Classification Search
None
See application file for complete search history.

(56) References Cited

U.S. PATENT DOCUMENTS

| | | |
|---|---|---|
| 4,144,258 A | 3/1979 | L'Eplattenier |
| 2011/0098309 A1 | 4/2011 | Look |

FOREIGN PATENT DOCUMENTS

| | | |
|---|---|---|
| WO | 99/01423 A1 | 1/1999 |
| WO | 01/41737 A2 | 6/2001 |
| WO | 2006/136008 A1 | 12/2006 |
| WO | WO 2006136008 A1 * | 12/2006 |
| WO | 2008/066887 A2 | 6/2008 |
| WO | 2011/057034 A2 | 5/2011 |
| WO | 2012/033938 A2 | 3/2012 |

OTHER PUBLICATIONS

CAPLUS 1969:96559.*
Zhi, Feng, Acta Crystallographica, Section E: Structure Reports, 2008.
Kline, Bioorganic & Medicinal Chemistry (2000), 8(1), 73-93.
Ainscough, Journal of Inorganic Biochemistry (1999), 77(3-4), 125-133.
Desal, Indian Journal of Heterocyclic Chemistry (1999), 8(4), 329-334.
Edward, Canadian Journal of Physiology and Pharmacology, (1997), 75(12), 1362-1368.
Richardson, D.R., Antimicrobial Agents and Chemotherapy (1997), 41(9), 2061-2063.
Richardson, D.R., Blood (1997), 89(8), 3025-3038.
Zhao, Journal of Medicinal Chemistry (1997), 40(6), 937-941.
Richardson, D.R., Blood (1995), 86(11), 4295-4306.
Katrolia, Hindustan Antibiotics Bulletin (1989), 31(3-4), 65-70.
Pagani, Farmaco, Edizione Scientifica (1969), 24(12), 997-1024.
Memorial Sloan-Kettering Cancer Center, PCT/US2012/064278, IPRP and WO of ISA (May 22, 2014).
Memorial Sloan-Kettering Cancer Center, PCT/US2012/064278, International Search Report (May 22, 2014).
Database Registry, Accession No. 328542-05-8, (Mar. 25, 2001), XP002691618.

* cited by examiner

*Primary Examiner* — Heidi Reese
(74) *Attorney, Agent, or Firm* — Heslin, Rothenberg, Farley & Mesiti, PC

(57) ABSTRACT

Methods for inhibiting the growth of ovarian cancer cells or other serosal cancer cells are disclosed. The method involves exposing the cells to a benzylidinebenzohydrazide of formula:

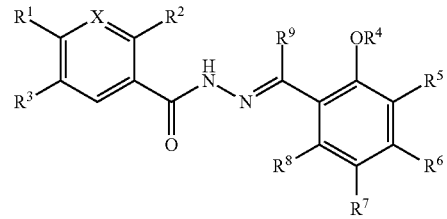

wherein X is carbon or nitrogen.

5 Claims, No Drawings

TREATMENT OF OVARIAN CANCER WITH BENZYLIDENEBENZOHYDRAZIDES

CROSS REFERENCE TO RELATED APPLICATIONS

This application is a national phase filing under 35 U.S.C. §371 of PCT International Application PCT/US2012/064278, filed Nov. 9, 2012, and published under PCT Article 21(2) in English as WO 2013/071001 on May 16, 2013. PCT/US2012/064278 claimed priority from U.S. provisional application 61/558,293, filed Nov. 10, 2011, the entire contents of each of which are incorporated herein by reference.

FIELD OF THE INVENTION

The invention relates to benzylidinebenzohydrazides that are useful for treating ovarian cancer and other types of serosal cancers.

BACKGROUND OF THE INVENTION

Ovarian cancer ranks fifth in cancer deaths among women and causes more deaths than any other gynecologic malignancy. It is estimated that in the United States 22,430 new cases will be diagnosed each year with 15,280 deaths. Ovarian carcinoma remains enigmatic in at least two important respects. First, the histological region of origin for this cancer remains obscure and second, an identifiable premalignant lesion that is generally recognized by cancer pathologists is yet to be defined. The majority (80%) of patients present with advanced stage disease with cancer cells throughout the abdominal cavity, leading directly to the high mortality (5 year survival rates 15-45%). In contrast, the survival rate for early stage disease, with malignancy confined to the ovary, is about 95%.

The median overall survival for patients with advanced ovarian cancer has improved from approximately 1 year in 1975 to currently in excess of 3 years. For subsets of patients having optimally debulked disease and receiving treatment with taxane- and platinum-based combination chemotherapy, survival now exceeds 5 years. However the disease course is one of remission and relapse requiring intermittent re-treatment. The presence of cancer cells in effusions within the serosal (peritoneal, pleural, and pericardial) cavities is a clinical manifestation of advanced stage cancer and is associated with poor survival. Tumor cells in effusions most frequently originate from primary carcinomas of the ovary, breast, and lung, and from malignant mesothelioma, a native tumor of this anatomic site. Unlike the majority of solid tumors, particularly at the primary site, cancer cells in effusions are not amenable to surgical removal and failure in their eradication is one of the main causes of treatment failure.

PCT WO2011/057034 suggests that serosal ovarian cancer stem cells (also called catena cells), which possess a glycocalyx (pericellular coat), may be the most drug resistant structure in ovarian cancer. Presumably due to the impermeability of the glycocalyx, catena cells appear resistant to many chemotherapeutic agents. It is important to discover compounds that can penetrate the glycocalyx and exert toxicity against ovarian cancer stem cells. Eradicating cancer stem cells (CSCs) would be expected to increase the efficiency of therapy for ovarian or other serosal cancers, including metastatic serosal cancer.

SUMMARY OF THE INVENTION

The compounds of the invention are useful as anticancer agents, particularly in the treatment of ovarian and other serosal cancers.

In one aspect, the invention relates to a method for inhibiting the growth of an ovarian cancer cell or other cancer cell with a pericellular coat comprising exposing said cell to a compound of formula I:

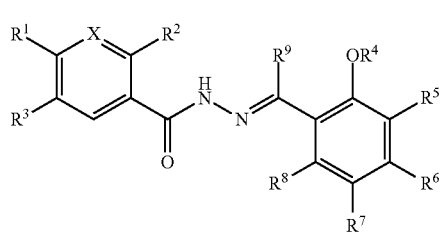

wherein:
$R^1$ is chosen from H, $CH_3$, Cl, Br, $CF_3$, $NO_2$ and dimethylpyrazolylmethyl;
$R^2$ is chosen from H, OH, $OCH_3$ and —NHC(=O)furanyl;
$R^3$ is chosen from H, $NO_2$ and pyrazolylmethyl
or $R^1$ and $R^3$ taken together form an optionally substituted five or six-membered ring;
$R^4$ is chosen from H and 4-chlorobenzoyl, and $R^4$ may additionally be $(C_5-C_8)$hydrocarbon when either $R^1$ is Br or both of $R^3$ and $R^{13}$ are $NO_2$;
$R^5$ is chosen from H, $CH_3$ and $OCH_3$;
$R^6$ is chosen from H, —$NR^{10}R^{11}$, —$OR^{12}$, and $CH_3$;
$R^7$ is H, or, when $R^5$ is $CH_3$ or $OCH_3$, $R^7$ may additionally be halogen or $CF_3$;
$R^8$ is hydrogen,
or any two adjacent $R^4$, $R^5$, $R^6$, $R^7$, $R^8$ or $R^9$ taken together form an optionally substituted five
or six-membered carbocyclic ring;
$R^9$ is chosen from H and $CH_3$;
$R^{10}$, $R^{11}$ and $R^{12}$ are independently chosen from H and $(C_1-C_8)$hydrocarbon; and
$R^{13}$ is chosen from H, $NO_2$, I and Cl.
X is $CR^{13}$; or, when $R^1$ is $CH_3$, X may additionally be N;
with the provisos that:
(a) when $R^5$ and $R^6$ taken together form a ring, at least one of $R^1$, $R^2$, $R^3$ and $R^4$ must be other than H;
(b) when $R^7$ and $R^8$ taken together form a ring, neither of $R^3$ and $R^{13}$ can be $NO_2$; and
(c) when both of $R^3$ and $R^{13}$ are $NO_2$, $R^5$ cannot be $OCH_3$.

In another aspect, the invention relates to a method for treating serosal cancer in a patient having serosal cancer, said method comprising administering to said patient a therapeutically effective amount of a compound of formula I.

In another aspect, the invention relates to a compound of formula:

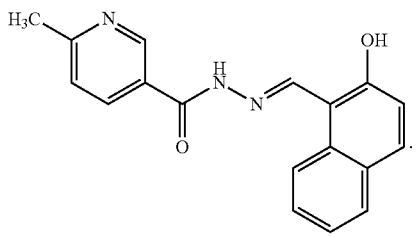 [SMILES: Cc1ccc(C(=O)N/N=C/c2c(O)ccc3ccccc23)cn1]

In another aspect, the invention relates to a pharmaceutical composition comprising a pharmaceutically acceptable carrier and a compound of formula:

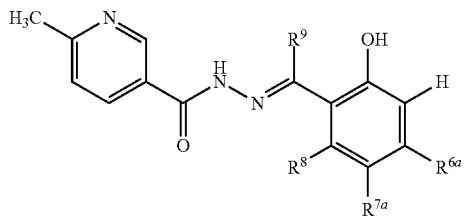

wherein:
$R^{6a}$ is chosen from H, —NCH$_3$)$_2$, —N(CH$_2$CH$_3$)$_2$, —OH, —OCH$_3$, and —OCH$_2$CH$_3$;
$R^{7a}$ and $R^8$ are hydrogen, or $R^{7a}$ and $R^8$ taken together may form an optionally substituted six-membered carbocyclic ring.

DETAILED DESCRIPTION OF THE INVENTION

The serosal cavity is a closed body cavity that includes and encloses the peritoneal, pleural, and pericardial cavities of the body, is fluid filled (serosal fluid) and is bounded by the serous membrane. Serosal cells are any cells originating from or found within the serosal cavity or forming or attaching to the serous membrane, and include, but are not limited to, ovarian, endothelial, stomach, intestinal, anal, pancreatic, liver, lung and heart cells. Serosal cancers include the primary cancers that arise within the serosal cavity and secondary cancers that arise by metastasis of other cancer cells into the serosal cavity. Major serosal cancers at different serosal sites include those in (1) pleural effusions, namely mesothelioma, bronchogenic lung cancer, breast cancer, bladder cancer, ovarian cancer, fallopian tube cancer, cervical cancer and sarcoma; (2) peritoneal effusions, namely ovarian cancer, fallopian tube cancer, gastric cancer, pancreatic cancer, colon cancer, renal cancer and bladder cancer; and (3) pericardial effusions, namely mesothelioma, bronchogenic lung cancer, breast cancer, bladder cancer, ovarian cancer, fallopian tube cancer, cervical cancer and sarcoma. The list is not exhaustive, and other cancers that metastasize to a serosal cavity and form tumors can be considered as "serosal cancers."

WO2011/057034 discloses a model of the catena-spheroid concept and the role of CSCs in the development of ovarian cancer. According to this model, the initial transformation of ovarian (or fallopian) epithelium progresses via an epithelial-mesenchymal and mesenchymal-catena transition. The catena cells lose all attachment to extracellular matrix or peritoneal mesothelium but remain attached to each other following each round of symmetric division. At this point, the catena is composed predominantly of CSCs. The catenae can release single cells that generate secondary catenae or form spheroids. The catenae can also roll up and form spheres which contain a >10 fold higher frequency of CSC than tumors growing as two-dimensional (2D) monolayers or solid tumors. Spheroids can release new catenae or can attach to the mesothelial wall of the peritoneum to form omental cakes. Catenae may be released from solid tumors by a mesenchymal-catena transition and may reenter the peritoneal ascites or penetrate into blood vessels leading to more distant metastasis. Hyaluronan is a major component of the glycocalyx, which is a predominant morphological feature of catenae and can be removed by treatment with hyaluronidase. The glycocalyx extends up to approximately 20 μm around the catena cells.

It has now been found that certain benzylidinebenzohydrazides are capable of penetrating the glycocalyx and inhibiting the growth of catena cells.

In one aspect, the invention relates to methods employing compounds of formula I:

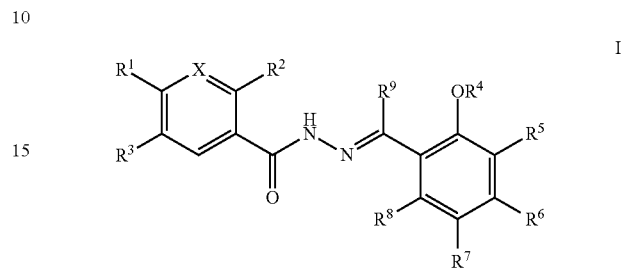

In some embodiments of the invention, the methods involve administration of compounds of the formula II:

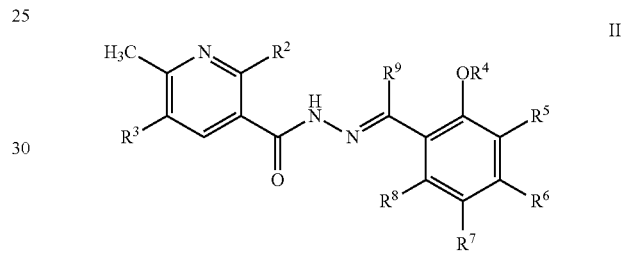

which is a subset of formula I. In these compounds, X is N and $R^1$ is CH$_3$. In some embodiments of subset II, $R^6$ may be —NR$^{10}$R$^{11}$ or $R^5$ and $R^6$ taken together may form a ring. When $R^5$ and $R^6$ together form an aromatic ring, $R^2$, $R^3$, $R^4$ and $R^9$ may be H. When $R^6$ is —NR$^{10}$R$^{11}$, $R^2$, $R^3$, $R^5$, $R^7$, $R^8$ and $R^9$ may be H and $R^{10}$ and $R^{11}$ may be methyl or ethyl.

In other embodiments of the invention, which form another subset of the compounds of formula I, the methods involve administration of compounds of the formula III:

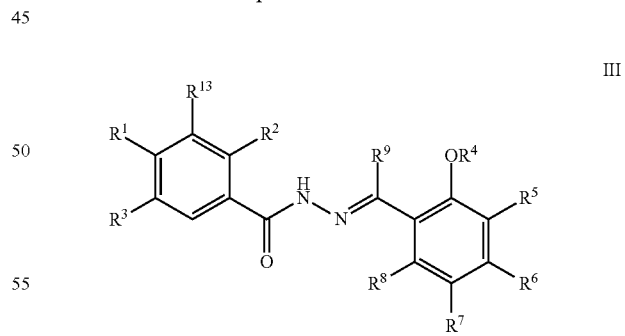

In these compounds, X is CR$^{13}$. In some embodiments, $R^7$ and $R^8$ taken together form an aromatic ring. In some embodiments $R^1$ and $R^3$ together form an aromatic ring and $R^2$ may be OCH$_3$. In other embodiments, $R^2$, $R^5R^6$, $R^9$ and $R^{13}$ are H and at least one of $R^1$ and $R^3$ is H. When at least one of $R^1$ and $R^3$ is H, the other of $R^1$ and $R^3$ may be pyrazolylmethyl, dimethylpyrazolylmethyl, nitro or H. When both of $R^1$ and $R^3$ are H, $R^4$ may be 4-chlorobenzoyl. When one of $R^1$ and $R^3$ is H and the other of $R^1$ and $R^3$ is chosen from pyrazolylmethyl, dimethylpyrazolylmethyl and nitro, then $R^4$ may be H. In some embodiments, $R^2$, $R^4$, $R^7$, $R^8$ and $R^{13}$ may be H, one of $R^1$ and $R^3$ may be $NO_2$ and the other of $R^1$ and $R^3$ may be H. In some embodiments, $R^5$ and $R^6$ taken together form an aromatic ring, whereas in others $R^5$ and $R^6$ are both H. In some embodiments $R^4$ is H and none of $R^1$, $R^3$, $R^5$, $R^6$, $R^7$, $R^8$ and $R^9$ forms a ring. In these compounds, $R^1$ may be H, $CH_3$, Cl, Br, $CF_3$ or $NO_2$. Further, $R^5$ may be H and $R^6$ may be H, $-N(CH_3)_2$, $-N(CH_2CH_3)_2$, $-OH$, $-OCH_3$, $-OCH_2CH_3$ or $CH_3$. In these compounds, $R^5$ may be $CH_3$ or $OCH_3$ and $R^7$ may be chloro, bromo, $CF_3$ or iodo. Also, when $R^1$ is H, $CH_3$, Cl, Br, $CF_3$ or $NO_2$, $R^2$ may additionally be $-NHC(=O)$ furanyl.

In other embodiments of formula III, $R^4$ may be $-C_6H_{13}$ and all of $R^2$, $R^3$, $R^5$, $R^6$, $R^7$, and $R^8$ may be H. Alternatively, $R^4$ may be benzyl or methylbenzyl, $R^6$ may be benzyl or methylbenzyl, all of $R^1$, $R^2$, $R^5$, $R^7$, and $R^8$ may be H and both of $R^3$ and $R^{13}$ may be $NO_2$.

Throughout this specification the terms and substituents retain their definitions.

Alkyl is intended to include linear or branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below; more preferred are $C_8$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an aryl ring attached to an alkyl residue in which the point of attachment to the parent structure is through the alkyl. Examples are benzyl, phenethyl and the like. Heteroarylalkyl means an alkyl residue attached to a heteroaryl ring, in which the point of attachment to the parent structure is through the alkyl. Examples include, e.g., pyridinylmethyl, pyrimidinylethyl and the like.

$C_1$ to $C_{10}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl, camphoryl and naphthylethyl.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means a cycloalkyl or aryl residue in which one to two of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. Substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, hydroxy, loweralkoxy, haloalkoxy, oxaalkyl, carboxy, nitro, amino, alkylamino, and/or dialkylamino. In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The compounds described herein contain double bonds and may also contain other centers of geometric asymmetry; unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. The compounds described herein may also contain, in a substituent Rx, one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques.

As used herein, and as would be understood by the person of skill in the art, the recitation of "a compound"—unless expressly further limited—is intended to include salts of that compound. In a particular embodiment, the term "compound of formula I" refers to the compound or a pharmaceutically acceptable salt thereof. For example, when X is nitrogen or $R^6$ is $-NR^{10}R^{10}$, the compounds of the invention may exist as salts, i.e. cationic species.

The term "pharmaceutically acceptable salt" refers to salts whose counter ion (anion) derives from pharmaceutically acceptable non-toxic acids including inorganic acids and organic acids. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^2H$, $^3H$, $^{11}C$, $^{13}C$, $^{14}C$, $^{15}N$, $^{35}S$, $^{18}F$, $^{36}C$, $^{125}I$, $^{124}I$ and $^{131}I$ respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formulae I and II of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus I for use in treating cancer where such use is not already in the possession of the public.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, intraperitoneally, intratumorally or subcutaneously.

Formulations include those suitable for oral, parenteral (including subcutaneous, intradermal, intramuscular, intravenous and intraarticular), rectal and topical administration. The compounds are preferably administered orally or by injection (intravenous, intramuscular, intraperitoneally, intratumorally or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient reporting one or more of the physiological symptoms of a disease, even though a diagnosis of this disease may not have been made.

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The compounds employed in the invention are commercially available, are known or may be synthesized by processes known in the art. For example, US published patent application 2011-0098309 describes the synthesis of 75 species of 2-hydroxyphenyl-methylenehydrazides. The disclosures of US 2011-0098309 from page 48 to 50 and page 53 to 57 and US 2006-0293292 page 11 are incorporated herein by reference. In general the synthesis may be schematically described as follows:

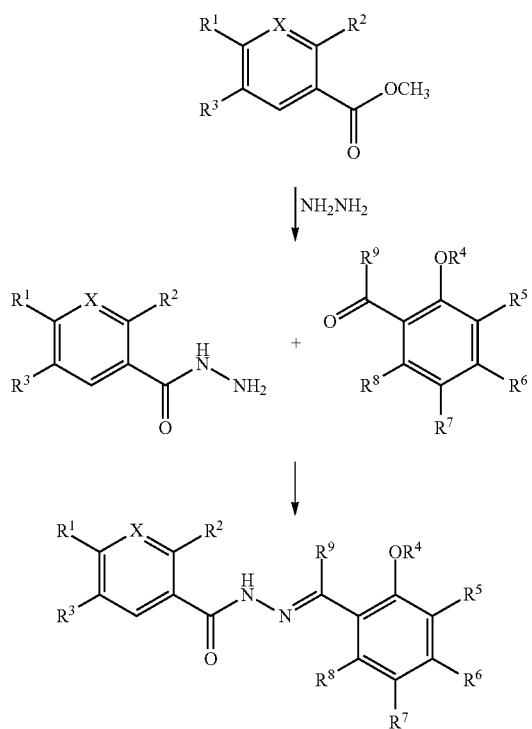

Twenty-one examples of compounds of the genus I have been prepared and tested according to the protocol described in WO2011/057034, which is recapitulated here. Ovcar3-GTL-derived catenae were tested for their ability to self-propagate in flat bottom 384-well microtiter plates (Corning). Cultures of Ovcar3-GTL catenae were mechanically or enzymatically dissociated to single cells. For mechanical dissociation, catena cultures were pipetted vigorously, an equal volume of M5-FCS media was added to decrease the viscosity, and the cells were pelleted. For enzymatic dissociation, catena cultures were incubated at 5 mg/ml collagenase IV (Invitrogen) for 10 min at 37° C. followed by centrifugation to pellet the cells. Cells were resuspended in M5-FCS to produce homogenous cultures of single cells which were seeded in 50 microliter aliquots per well at the indicated cell densities and grown for 6 days before addition of test compounds or other reagents.

To assess cell growth, cells were observed under the microscope and manually counted using a hematocytometer or were treated with alamarBlue by adding 1/10 volume of alamarBlue reagent directly to the culture medium, incubating the cultures for a further 48 hours at 37° C. and measuring the fluorescence or absorbance. Both spectroscopic methods gave comparable results. The amount of fluorescence or absorbance is proportional to the number of living cells and corresponds to the cells metabolic activity. Fluorescence measurement is more sensitive than absorbance measurement and is measured by a plate reader using a fluorescence excitation wavelength of 540-570 nm (peak excitation is 570 nm) and reading emission at 580-610 nm (peak emission is 585 nm). Absorbance of alamarBlue0 is monitored at 570 nm, using 600 nm as a reference wavelength. Larger fluorescence emission intensity (or absorbance) values correlate to an increase in total metabolic activity from cells.

Because the components of the pericellular glycocalyx were significantly removed prior to cell seeding by mechanical or enzymatic dissociation of catena, the optimal time for adding compounds to ensure that the catenae had an established glycocalyx is 3-6 days after seeding. In WO2011/057034 it was shown that catena were resistant to 21 out of 23 known anticancer agents. The formation of glycocalyx conferred more than 8,000,000-fold resistance in catenae to paclitaxel, fludelone and 9-10dEpoB. All 21 of the benzylidinebenzohydrazides described below were found active in this screen, indicating that, unlike most known anticancer agents, the benzylidinebenzohydrazides are able to penetrate the glycocalyx.

Compounds tested and found effective were:

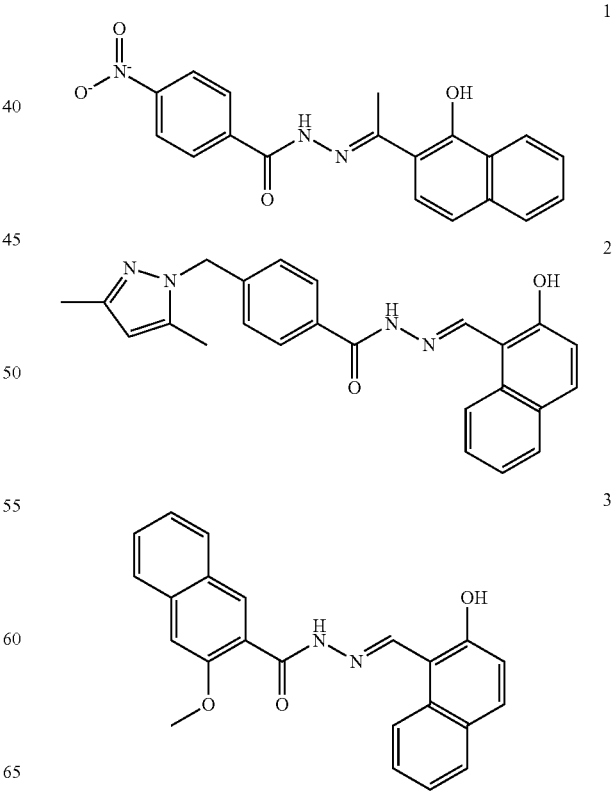

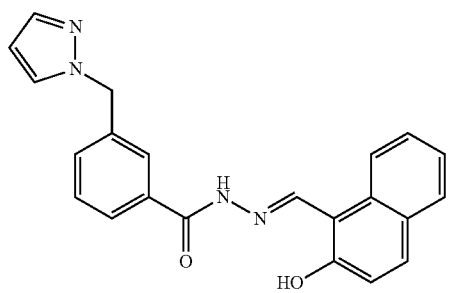
4
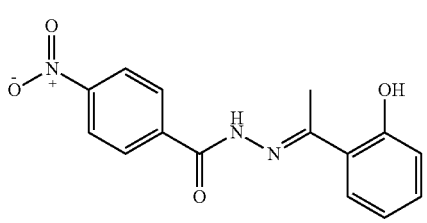
5
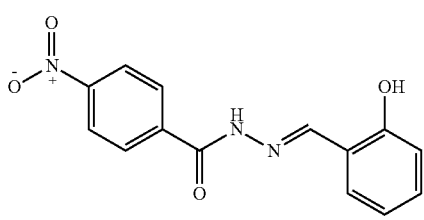
6
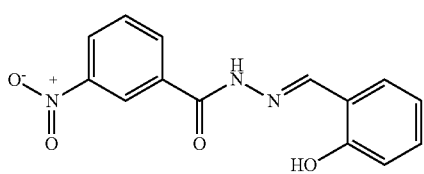
7
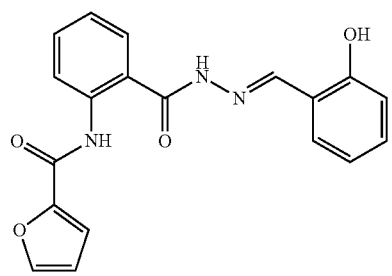
8
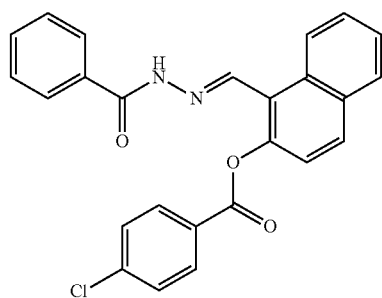
9
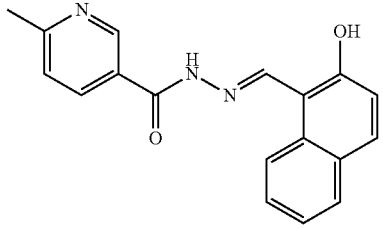
10
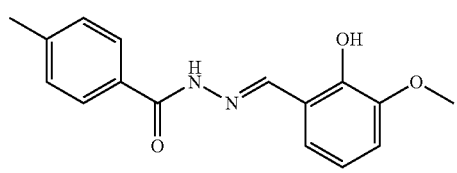
11
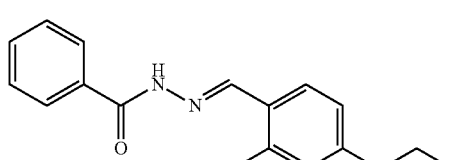
12
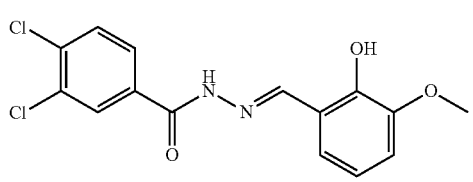
13
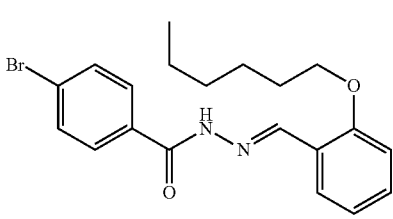
14
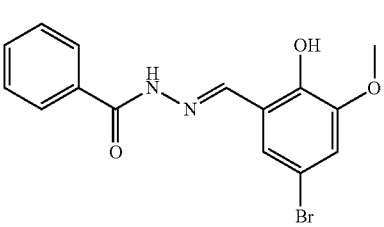
15
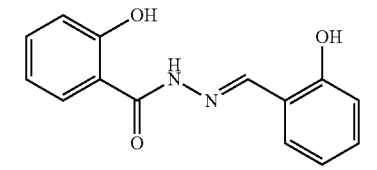
16
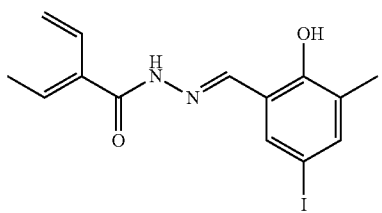
17

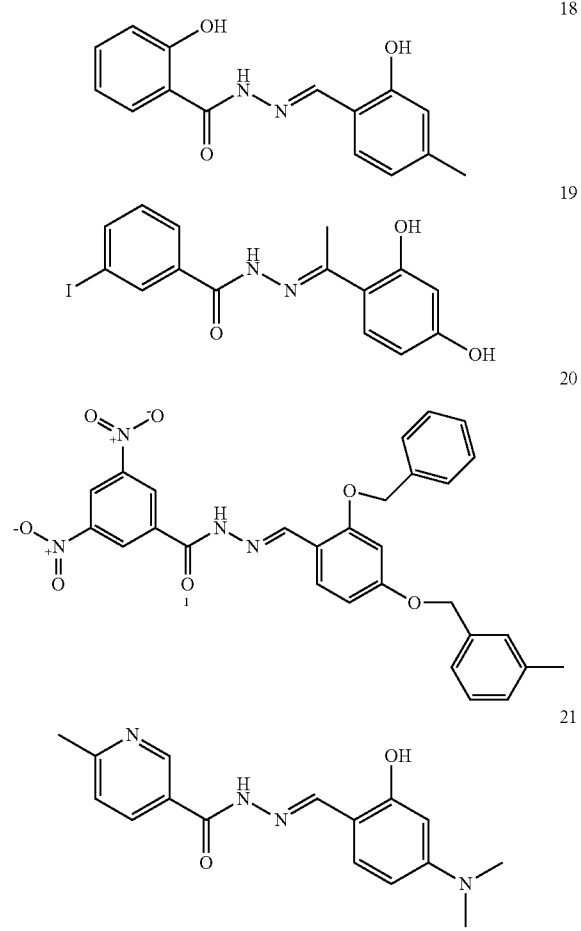

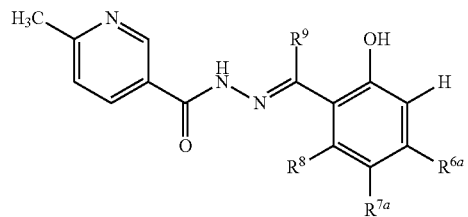

The compound designated example 10 above was tested in vivo for toxicity in NSG mice. As used herein, NSG and NSG mice mean the NOD scid gamma (NSG) mice, or an equivalent, available from The Jackson Laboratory and which are the NOD.Cg-Prkdc$^{scid}$ Il2rg$^{tm1Wjl}$/SzJ JAX® Mice strain. The NSG mice were injected intraperitoneally with 1, 2.5, 5, 10, 20 or 40 mg/kg of the compound designated example 10 above for once or three times a week for 4 weeks. The compound designated example 10 above showed no overt toxicity in any concentrations or at any drug administration schedules.

The invention claimed is:

1. A pharmaceutical composition comprising a pharmaceutically acceptable carrier and a compound of formula:

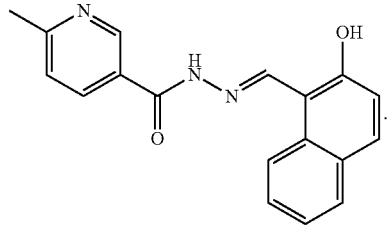

wherein:
$R^{6a}$ is chosen from H, —N(CH$_3$)$_2$, —N(CH$_2$CH$_3$)$_2$, —OH, —OCH$_3$, and —OCH$_2$CH$_3$;
$R^{7a}$ and $R^8$ are hydrogen, or $R^{7a}$ and $R^8$ taken together may form an optionally substituted six-membered carbocyclic ring; and
$R^9$ is chosen from H and CH$_3$.

2. A composition according to claim 1 wherein $R^{6a}$ is —N(CH$_3$)$_2$ or —N(CH$_2$CH$_3$)$_2$.

3. A composition according to claim 1 wherein $R^{7a}$ and $R^8$ are hydrogen.

4. A composition according to claim 1 wherein $R^{7a}$ and $R^8$ taken together form an aromatic ring.

5. A composition according to claim 4 wherein said compound has formula:

* * * * *